United States Patent [19]

Jones et al.

[11] Patent Number: 4,654,338
[45] Date of Patent: Mar. 31, 1987

[54] 1,2,4-THIADIAZINES

[75] Inventors: Stuart D. Jones, Cricklade; Wilfred R. Tully, Cirencester; Peter D. Kennewell, Swindon, all of Great Britain

[73] Assignee: Roussel Uclaf, Paris, France

[21] Appl. No.: 716,050

[22] Filed: Mar. 26, 1985

[30] Foreign Application Priority Data

Apr. 2, 1984 [GB] United Kingdom ................ 8408447

[51] Int. Cl.$^4$ ................ C07D 285/18; C07D 417/04; C07D 413/04; A61K 31/54
[52] U.S. Cl. ........................................ 514/222; 544/8
[58] Field of Search ............................ 544/8; 514/222

[56] References Cited

FOREIGN PATENT DOCUMENTS 2159149 11/1985 United Kingdom .................... 544/8

Primary Examiner—John M. Ford
Attorney, Agent, or Firm—Bierman & Muserlian

[57] ABSTRACT

Novel 1,2,4-thiadiazines of the formula

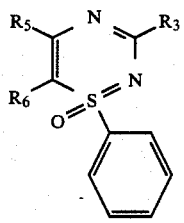

I wherein $R_3$ is selected from the group consisting of hydrogen, —OH, —CF$_3$, alkyl, alkoxy and alkylthio of 1 to 6 carbon atoms, cycloalkyl of 3 to 6 carbon atoms optionally substituted with alkyl of 1 to 6 carbon atoms and

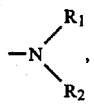

$R_1$ and $R_2$ are individually selected from the group consisting of hydrogen and alkyl of 1 to 3 carbon atoms or taken together with the nitrogen to which they are attached form a saturated heterocycle of 4 to 8 carbon atoms optionally containing a heteroatom of the group consisting of —O—, —S— and

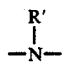

and R' is hydrogen or alkyl of 1 to 3 carbon atoms, $R_5$ is

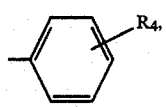

$R_4$ is selected from the group consisting of hydrogen, halogen and alkyl and alkoxy of 1 to 3 carbon atoms, $R_6$ is selected from the group consisting of hydrogen, halogen and alkyl of 1 to 3 carbon atoms with the proviso that $R_6$ may represent halogen only when $R_3$ is hydrogen, —OH, alkyl and alkoxy of 1 to 6 carbon atoms or cycloalkyl of 3 to 6 carbon atoms optionally substituted with alkyl of 1 to 6 carbon atoms and their non-toxic, pharmaceutically acceptable acid addition salts having a remarkable anxiolytic activity and novel intermediates.

30 Claims, No Drawings

1,2,4-THIADIAZINES

OBJECTS OF THE INVENTION

It is an object of the invention to provide the novel 1,2,4-thiadiazines of formula I and their non-toxic, pharmaceutically acceptable acid addition salts and a process and novel intermediates for their preparation.

It is another object of the invention to provide novel anxiolytic compositions and a novel method of treating anxiety in warm-blooded animals.

These and other objects and advantages of the invention will become obvious from the following detailed description.

THE INVENTION

The novel compounds of the invention are selected from the group consisting of 1,2,4-thiadiazines of the formula

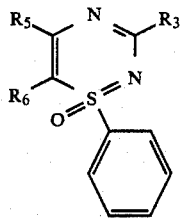

I wherein $R_3$ is selected from the group consisting of hydrogen, —OH, —CF$_3$, alkyl, alkoxy and alkylthio of 1 to 6 carbon atoms, cycloalkyl of 3 to 6 carbon atoms optionally substituted with alkyl of 1 to 6 carbon atoms and

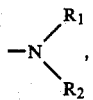

$R_1$ and $R_2$ are individually selected from the group consisting of hydrogen and alkyl of 1 to 3 carbon atoms or taken together with the nitrogen to which they are attached form a saturated heterocycle of 4 to 8 carbon atoms optionally containing a heteroatom of the group consisting of —O—, —S— and

and R' is hydrogen or alkyl of 1 to 3 carbon atoms, $R_5$ is

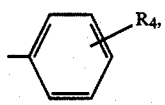

$R_4$ is selected from the group consisting of hydrogen, halogen and alkyl and alkoxy of 1 to 3 carbon atoms, $R_6$ is selected from the group consisting of hydrogen, halogen and alkyl of 1 to 3 carbon atoms with the proviso that $R_6$ is halogen only when $R_3$ is hydrogen, —OH, alkyl and alkoxy of 1 to 6 carbon atoms or cycloalkyl of 3 to 6 carbon atoms optionally substituted with alkyl of 1 to 6 carbon atoms and their non-toxic, pharmaceutically acceptable acid addition salts.

Since the compounds of formula I possess an asymmetric sulfur atom, they can exist in enantiomeric forms and the invention includes racemic and other mixtures thereof as well as the individual enantiomers.

Examples of alkyl of 1 to 6 carbon atoms are methyl, ethyl, propyl, isopropyl, n-butyl, sec.-butyl, tert.-butyl, pentyl and hexyl and examples of alkoxy and alkylthio of 1 to 6 carbon atoms are methoxy, ethoxy, propoxy, isopropoxy, methylthio, ethylthio, propylthio and isopropylthio. Examples of halogen are chlorine, bromine, iodine and fluorine.

Examples of saturated heterocycle of 4 to 8 carbon atoms optionally containing —O—, —S— and

are pyrrolidino, piperidino, morpholino, thiomorpholino, piperazin-1-yl and 4-alkyl-piperazin-1-yl with 1 to 3 alkyl carbon atoms. Examples of cycloalkyl of 3 to 6 carbon atoms optionally substituted with alkyl of 1 to 3 carbon atoms are cyclopropyl, cyclobutyl, cyclopentyl and cyclohexyl, all optionally substituted with methyl, ethyl, propyl or isopropyl.

Examples of suitable acids for the formation of non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, propionic acid, formic acid, benzoic acid, maleic acid, fumaric acid, succinic acid, tartaric acid, citric acid, oxalic acid, glyoxylic acid, aspartic acid, alkane sulfonic acids such as methane sulfonic acid and aryl sulfonic acids such as benzene sulfonic acid.

Among the preferred compounds of the invention of formula I are those wherein $R_3$ is hydrogen, hydroxy, —CF$_3$, alkyl, alkoxy or alkylthio of 1 to 6 carbon atoms, cycloalkyl of 3 to 6 carbon atoms optionally substituted with alkyl of 1 to 6 carbon atoms, —NH$_2$, mono- and di alkylamines of 1 to 3 alkyl carbon atoms, pyrrolidino, piperidino, morpholino, thiomorpholino, piperazin-1-yl or 4-alkyl-piperazin-1-yl of 1 to 3 alkyl carbon atoms, those wherein $R_5$ is phenyl, chlorophenyl, methylphenyl or methoxyphenyl and those wherein $R_6$ is hydrogen, bromine or methyl and their non-toxic, pharmaceutically acceptable acid addition salts.

More preferred are the compounds of formula I wherein $R_3$ is hydrogen, methyl, —CF$_3$, —OH, ethoxy, methylthio, ethylthio, —NH$_2$, piperidino or 4-methylpiperazin-1-yl, wherein $R_5$ is phenyl, o-chlorophenyl, p-methylphenyl or p-methoxyphenyl or wherein $R_6$ is hydrogen, bromine or methyl and their non-toxic, pharmaceutically acceptable acid addition salts.

Examples of specific preferred compounds of formula I are 1,5-diphenyl-1H-1,2,4-thiadiazine-1-oxide, 1,5-diphenyl-6-methyl-1H-1,2,4-thiadiazine-1-oxide, 1,5-diphenyl-3-methyl-1H-1,2,4-thiadiazine-1-oxide, 6-bromo-1,5-diphenyl-1H-1,2,4-thiadiazine-1-oxide, 1,5-diphenyl-3-methoxy-1H-1,2,4-thiadiazine-1-oxide, (−)-1,5-diphenyl-1H-1,2,4-thiadiazine-1-oxide and (+)-3-methoxy-1,5-diphenyl-1H-1,2,4-thiadiazine-1-oxide and their non-toxic, pharmaceutically acceptable acid addition salts.

The novel process of the invention for the preparation of the compounds of formula I wherein $R_3$ and $R_6$ are individually hydrogen or alkyl of 1 to 3 carbon atoms comprises reacting a compound of the formula

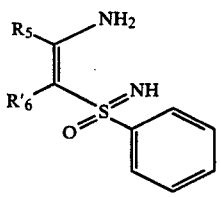

wherein R'$_6$ is hydrogen or alkyl of 1 to 3 carbon atoms and R$_5$ is as defined above with a compound of the formula

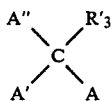

wherein A, A' and A" are individually selected from the group consisting of ethoxy and dimethylamino and R'$_3$ is hydrogen or alkyl of 1 to 3 carbon atoms and, if desired, subsequently isolating and/or salifying the compound of formula I thus obtained.

The reaction of the compound of formula II with the compound of formula III is preferably carried out in an organic solvent such as dimethylformamide at a temperature between room temperature and the reflux temperature of the reaction mixture.

The process of the invention for the preparation of compounds of formula I wherein R$_3$ is selected from the group consisting of —CF$_3$, alkyl of 1 to 6 carbon atoms and cycloalkyl of 3 to 6 carbon atoms optionally substituted with alkyl of 1 to 6 carbon atoms and R$_6$ is hydrogen or alkyl of 1 to 3 carbon atoms comprises reacting a compound of formula II with an acid chloride of the formula

or an acid anhydride of the formula

wherein R"$_3$ is —CF$_3$, alkyl of 1 to 6 carbon atoms or cycloalkyl of 3 to 6 carbon atoms optionally substituted with alkyl of 1 to 6 carbon atoms, preferably in the presence of an organic base such as triethylamine in an organic solvent such as dichloromethane to obtain a corresponding compound of formula I.

The process of the invention for the preparation of a compound of formula I wherein R$_3$ is —OH comprises thermally cyclizing a compound of the formula

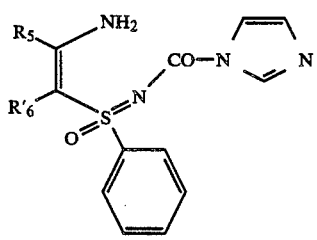

wherein R$_5$ and R'$_6$ have the above definitions and, if desired, subsequently isolating and/or salifying the compound of formula I wherein R$_3$ is hydroxy thus obtained.

The process of the invention for the preparation of compounds of formula I wherein R$_1$ is alkoxy or alkylthio of 1 to 3 carbon atoms or

comprises reacting a compound of the formula

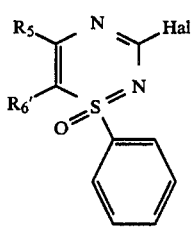

wherein Hal is halogen and R$_5$ and R'$_6$ have the above definitions with an amine of the formula

wherein R$_1$ and R$_2$ have the above definitions or with an alcohol of the formula Alk-OH or an alkylthio of the formula Alk-SH wherein Alk has the above definitions and if desired, isolating and/or salifying the resulting compound of the formula I. The latter two reactions are preferably effected in the presence of a base.

The compounds of formula IV may be prepared by reacting a compound of formula II with a N,N'-carbonyldiimidazol of the formula

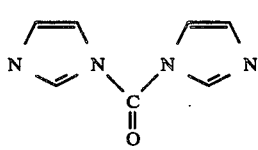

and the compound of formula IV may be isolated before cyclization or may be cyclized without isolation. The reaction with the compounds of formulae II and III$_A$ is preferably effected in an organic solvent such as chloromethane and the thermal cyclization of the compound of formula IV is preferably effected with heating up to reflux.

The compounds of formula V may be prepared by halogenation of a compound of formula I wherein R$_3$ is —OH and the halogenating agent is preferably a brominating agent or a chlorinating agent such as phosphorus oxylchloride.

The reaction of the compound of formula V with an amine of the formula

is preferably effected in the presence of a lower alkanol such as ethanol and the reaction with an alkanol of 1 to 6 carbon atoms is preferably effected in the presence of an alkali metal carbonate such as sodium carbonate. The reaction of the compound of formula V with an alkylthiol of 1 to 6 carbon atoms is preferably effected in the presence of an alkali metal hydride such as sodium hydride in an organic solvent such as dimethylformamide or tetrahydrofuran.

For the preparation of a compound of formula I wherein $R_3$ is hydrogen, —OH, alkyl or alkoxy of 1 to 6 carbon atoms or cycloalkyl of 3 to 6 carbon atoms optionally substituted with alkyl of 1 to 6 carbon atoms and $R_6$ is halogen, a compound of formula I wherein $R_3$ has the said definition and $R_6$ is hydrogen is halogenated, preferably with a halogen in an organic solvent such as chloroform.

For the preparation of compounds of formula I wherein $R_3$ is an anino group, a compound of formula II is reacted with cyanogen bromide, preferably in the presence of sodium hydride in an organic solvent such as tetrahydrofuran.

The compounds of formula I have a basic character and may be converted into their acid addition salts by known methods such as reacting the compound of formula I with a substantially stoichiometric amount of the acid.

The compounds of formula I may be obtained in an optically active form from any one of the above processes by starting with the optically active compound of formulae II or IV or by resolution of the racemate of compounds of formula I by conventional methods.

The intermediates of formulae IV and V are novel and are an object of the invention as well as the compounds of formula II. The compounds of formula II may be prepared by reacting an aryl-nitrile of the formula $R_5$—CN wherein $R_5$ has the above definition with an alkylphenyl sulfoximine dianion of the formula

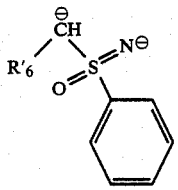

wherein $R'_6$ has the above definition.

The novel anxiolytic compositions of the invention are comprised of an anxiolytically effective amount of at least one compound of formula I or its non-toxic, pharmaceutically acceptable acid addition salts and an inert pharmaceutical carrier or excipient. The compositions may be in the form of tablets, dragees, capsules, gelatin capsules, granules, suppositories or injectable solutions or suspensions prepared in the usual manner.

Examples of suitable excipients are talc, arabic gum, lactose, starch, magnesium stearate, cocoa butter, aqueous and non-aqueous vehicles, animal or vegetable fats, paraffin derivatives, glycols, various wetting agents, dispersents or emulsifiers and preservatives.

The anxiolytic compositions of the invention are useful for the treatment of anxiety states, chronic anxiety with agitation, irritability, aggression, anxiety with insomnia and muscular tension and distress.

Among the preferred compositions of the invention are those wherein the active compound is selected from the group consisting of 1,5-diphenyl-1H-1,2,4-thiadiazine-1-oxide, 1,5-diphenyl-6-methyl-1H-1,2,4-thiadiazine-1-oxide, 1,5-diphenyl-3-methyl-1H-1,2,4-thiadiazine-1-oxide, 6-bromo-1,5-diphenyl-1H,1,2,4-thiadiazine-1-oxide, 3-methoxy-1,5-diphenyl-1H-1,2,4-thiadiazine-1-oxide, (—)-1,5-diphenyl-1H-1,2,4-thiadiazine-1-oxide and (+) 3-methoxy-1,5-diphenyl-1H-1,2,4-thiadiazine-1-oxide, and their non-toxic, pharmaceutically acceptable acid addition salts.

The novel method of the invention for relieving anxiety in warm-blooded animals, including humans, comprises administering to warm-blooded animals an anxiolytically effective amount of at least one compound of formula I or its non-toxic, pharmaceutically acceptable acid addition salts. The compounds may be administered orally, rectally or parenterally and the usual daily dose is depending upon the condition treated, the specific compound and the method of administration. For example, the oral dose may be 0.001 to 2.5 mg/kg, per day for adult human treatment.

In the following examples there are described several preferred embodiments to illustrate the invention. However, it should be understood that the invention is not intended to be limited to the specific embodiments. The following abbreviations are used therein:

EtOAc: ethyl acetate
TMS: tetramethylsilane
ppm: parts per million
IR: infra-red spectrum
Alk—OH: a $C_{1-3}$ alkanol
m.p.: melting point
M.Wt: molecular weight
OEt: ethoxy
DMSO: dimethylsulfoxide
DMF: N,N-dimethylformamide
THF: tetrahydrofuran

EXAMPLE 1

1,5-diphenyl-1H-1,2,4-thiadiazine-1-oxide

Step A: S-(2-aminostyryl)-S-phenyl-sulfoximine

To a solution of 8.3 g (0.053 mole) of methyl phenyl sulfoximine in 400 ml of dry tetrahydrofuran at 0° C. was added 1.4M (0.13 mol) butyl lithium in hexane to obtain a clear yellow solution. 15 ml (0.172 mole) of benzonitrile were added and the mixture was stirred for 30 minutes. 100 ml of saturated sodium chloride solution were added and the organic layer was separated, dried over magnesium sulfate and evaporated to an oil. The crude oil was triturated with petrol-ether (40° C.-60° C.) and then was chromatographed over silica. Elution with $CH_2Cl_2$, then a 1—1 $CH_2Cl_2$: EtOAc mixture yielded 8.8 g (64% yield) of pure S-(2-aminostyryl)-S-phenyl sulfoximine melting at 95°–96° C. after crystallization from ether.

Step B: 1,5-diphenyl-1H-1,2,4-thiadiazine-1-oxide

To a solution of 2 g (7.75 mmole) of S-(2-aminostyryl)-S-phenyl sulfoximine in 20 ml of dimethylformamide was added 1 g (8.5 mmole) of dimethylformamide dimethyl acetal and the mixture was heated at 80° C. for 15 minutes. The mixture was then cooled and diluted with 100 ml of ethyl acetate. The organic phase was washed 3 times with 75 ml of water, dried over magnesium sulfate and evaporated to an oil which was crystallized from ether/petrol to obtain 1.67 g (80%) of 1,5-diphenyl-1H-1,2,4-thiadiazine-1-oxide melting at 110°–111° C.

Analytical data are given in Table II below.

EXAMPLE 2

1-phenyl-5-(4-tolyl)-1H-1,2,4-thiadiazine-1-oxide

Using the procedure of Example 1, the appropriate benzonitrile was reacted to form S-[2-amino-2-(4-methylphenyl)-vinyl]-S-phenyl-sulfoximine which was then reacted to form 1-phenyl-5-(4-tolyl)-1H-1,2,4-thiadiazine-1-oxide.

EXAMPLE 3

5-(4-methoxyphenyl)-1-phenyl-1H-1,2,4-thiadiazine-1-oxide

Using the procedure of Example 1, the appropriate benzonitrile was reacted to form S-[2-amino-2-(4-methoxyphenyl)-vinyl]-S-phenyl-sulfoximine which was then reacted to form 5-(4-methoxyphenyl)-1-phenyl-1H-1,2,4-thiadiazine-1-oxide.

EXAMPLE 4

5-(2-chlorophenyl)-1-phenyl-1H-1,2,4-thiadiazine-1-oxide

Using the procedure of Example 1, the appropriate benzonitrile was reacted to obtain S-[2-amino-2-(2-chlorophenyl)-vinyl]-S-phenyl-sulfoximine which was then reacted to obtain 5-(2-chlorophenyl)-1-phenyl-1H-1,2,4-thiadiazine-1-oxide.

EXAMPLE 5

1,5-diphenyl-6-methyl-1H-1,2,4-thiadiazine-1-oxide

Using the procedure of Example 1, the appropriate benzonitrile was reacted to obtain S-(2-amino-1-methyl-styryl)-S-phenylsulfoximine which was then reacted to form 1,5-diphenyl-6-methyl-1H-1,2,4-thiadiazine-1-oxide.

EXAMPLE 6

1,5-diphenyl-3-methyl-1H-1,2,4-thiadiazine-1-oxide

Using the procedure of Step B of Example 1, the S-(2-aminostyryl)-S-phenyl-sulfoximine of Example 1 Step A was reacted with dimethyl acetamide dimethyl acetal to obtain 1,5-diphenyl-3-methyl-1H-1,2,4-thiadiazine-1-oxide.

The yield, melting parts and analytical data for the examples are reported in the following Tables.

EXAMPLE 7

3-hydroxy-1,5-diphenyl-1H-1,2,4-thiadiazine-1-oxide

To a solution of 12 g (0.047 mole) of S-(2-aminostyryl)-S-phenyl sulfoximine in 150 ml of dichloromethane was added 16.2 g (0.1 mole) of N,N'-carbonylidiimidazole and the mixture was stirred at ambient temperature for 48 hours before reducing to an oil. Column chromatography over silica and elution with 10% ethyl acetate in chloroform gave 15.6 g of an intermediate urea (95%) melting at 170°–171° C. (chloroform).

15.4 g (0.046 mole) of urea were heated at 200° C. in 60 ml of Dowthern A for 30 minutes and was cooled and diluted with 300 ml of ether. The product was filtered off, washed with ether and then a little chloroform and dried to obtain 12.1 g (89% i.e. 84% overall) of 3-hydroxy-1,5-diphenyl-1H-1,2,4-thiadiazine-1-oxide melting at 304°–305° C. after crystallization from methanol.

Analytical data are given in Table II below.

EXAMPLE 8

3-amino-1,5-diphenyl-1H-1,2,4-thiadiazine-1-oxide

To a solution of 2.58 g (10 mmole) of S-(2-aminostyryl)-S-phenyl sulfoximine in 100 ml of dry tetrahydrofuran was added 300 mg (10 mmole) of sodium hydride (80% dispersion in oil) and followed by 1.06 g (10 mmole) of cyanogen bromide. The mixture was stirred for 24 hours and was then washed twice with an aqueous sodium chloride solution and evaporated to an oil. The residue was chromatographed over silica gel and eluted with $CH_2Cl_2$, then 1:1 mixture of $CH_2Cl_2$:ethyl acetate to obtain 0.58 g (21%) of 3-amino-1,5-diphenyl-1H-1,2,4-thiadiazine-1-oxide melting at 169°–170° C. after crystallization from ethyl acetate.

Analytical data are given in Table II below.

EXAMPLE 9

3-amino-1,5-diphenyl-1H-1,2,4-thiadiazine-1-oxide

Step A:

3-chloro-1,5-diphenyl-1H-1,2,4-thiadiazine-1-oxide

A solution of 13.84 g (0.049 mole) of 3-hydroxy-1,5-diphenyl-1H-1,2,4-thiadiazine-1-oxide of Example 7 in 50 ml of phosphorus oxychloride was refluxed for 30 minutes and then excess reagent was evaporated under vacuum. The residue was taken up in chloroform and the solution was washed once with water, dried over magnesium sulfate and evaporated to an oil. The residue crystallized on trituration with ethanol to obtain 10.8 g (73%) of 3-chloro-1,5-diphenyl-1H-1,2,4-thiadiazine-1-oxide melting at 117°–118° C.

Step B:

3-amino-1,5-diphenyl-1H-1,2,4-thiadiazine-1-oxide

To 75 ml of saturated a solution of ammonia in ethanol was added 3 g (0.01 mole) of 3-chloro-1,5-diphenyl-1H-1,2,4-thiadiazine-1-oxide and the mixture was heated in an autoclave at 100° C. for 3 hours. The mixture was cooled, poured into water and the product was filtered off, washed with water and dried to obtain 2.6 g (93%) of 3-amino-1,5-diphenyl-1H-1,2,4-thiadiazine-1-oxide melting at 169°–170° C.

Analytical data are given in Table II below.

EXAMPLES 10 TO 12

Using the procedure of Step B of Example 9 and starting from 3-chloro-1,5-diphenyl-1H-1,2,4-thiadiazine-1-oxide and the appropriate amine of formula

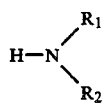

or alcohol (in presence of base) of formula Alk—OH, the following compounds were prepared. The reaction with an alcohol of formula Alk—OH required the presence of a base.

EXAMPLE 10

1,5-diphenyl-3-(N-piperidino)-1H-1,2,4-thiadiazine-1-oxide.

EXAMPLE 11

3-[1-(4-methylpiperazinyl)]-1,5-diphenyl-1H-1,2,4-thiadiazine-1-oxide.

EXAMPLE 12

3-ethoxy-1,5-diphenyl-1H-1,2,4-thiadiazine-1-oxide.
Analytical data are given in Table II below.

EXAMPLE 13

6-bromo-1,5-diphenyl-1H-1,2,4-thiadiazine-1-oxide

To a solution of 4.5 g (16 mmole) of 1,5-diphenyl-1H-1,2,4-thiadiazine-1-oxide of Example 1 in 225 ml of chloroform was added over 20 minutes a solution of 2.8 g, (7.5 mmole) of bromine in 25 ml of chloroform. After the addition was complete, the mixture was stirred for 30 minutes before reducing to an oil which was subjected to flash chromatography ($SiO_2$, petrol:-chloroform 1:1) to obtain 4.2 g of (73%) 6-bromo-1,5-diphenyl-1H-1,2,4-thiadiazine-1-oxide melting at 135°–136° C. after crystallization from ethyl acetate/ether.

Analytical data are given in Table II below.

EXAMPLE 14

1,5-diphenyl-3-methoxy-1H-1,2,4-thiadiazine-1-oxide

Using the procedure of Example 12, methanol as the solvent and reagent and sodium carbonate as the base were reacted to obtain 1,5-diphenyl-3-methoxy-1H-1,2,4-thiadiazine-1-oxide.

EXAMPLE 15

1,5-diphenyl-3-methylthio-1H-1,2,4-thiadiazine-1-oxide

Into a suspension of 1 g (33.3 mmole) of petrol-washed sodium hydride (80% dispersion in oil) in DMF was bubbled gaseous methanethiol until a clear solution resulted. To this preparation was added a solution of 3 g (10 mmole) of 3-chloro-1,5-diphenyl-1H-1,2,4-thiadiazine-1-oxide in DMF and the mixture was stirred for 1 hour at room temperature before being diluted with ethyl acetate and washed with water. The oil obtained by evaporation of the organic solvent was crystallized from dichloromethane-ether to obtain 2.32 g (74%) of 1,5-diphenyl-3-methylthio-1H-1,2,4-thiadiazine-1-oxide melting at 148°–150° C. after crystallization from dichloromethane-ether.

EXAMPLE 16

1,5-diphenyl-3-ethylthio-1H-1,2,4-thiadiazine-1-oxide

Using the procedure of Example 15, THF as solvent and ethanethiol as reagent were reacted to obtain 1,5-diphenyl-3-ethylthio-1H-1,2,4-thiadiazine-1-oxide.

EXAMPLE 17

1,5-diphenyl-3-trifluoromethyl-1H-1,2,4-thiadiazine-1-oxide

To a solution of 3 g (12 mmole) of S-(2-aminostyryl)-S-phenyl-sulfoximine in 100 ml of dichloromethane was added 1.33 g (13 mmole) of triethylamine and 2.77 g (13 mmole) of trifluoroacetic anhydride and the mixture was stirred for 2 hours at room temperature. The solvent was removed in vacuo and the resultant oil taken up in 100 ml of toluene. 0.4 g (3 mmole) of 1,5-diazabicyclo[4.3.0]non-5-ene was added and the mixture was refluxed for 2 hours. Removal of solvent in vacuo and column chromatography ($SiO_2$ petrol/dichloromethane) yielded 1.6 g (70%) of 1,5-diphenyl-3-trifluoromethyl-1H-1,2,4-thiadiazine-1-oxide melting at 136°–137° C. after crystallization from ether-petrol.

EXAMPLE 18

(−)-1,5-diphenyl-1H-1,2,4-thiadiazine-1-oxide

Step A: (+)-S-methyl-S-phenyl-sulfoximine (+)-S-methyl-S-phenyl-sulfoximine was prepared as described by Johnson et al [J. Am. Chem. Soc., 1973, Vol. 95 [22], 7418-23] to give optically pure product with a specific rotation of $[\alpha]_D^{20} = +36.7°$ (c=4, acetone).

Step B: (−)-1,5-diphenyl-1H-1,2,4-thiadiazine-1-oxide

Using the methods described for the preparation of S-(2-aminostyryl)-S-phenyl-sulfoximine (Example 1) and 1,5-diphenyl-1H-1,2,4-thiadiazine-1-oxide (Example 1), 5.5 g (35 mmole) of (+)-S-methyl-S-phenyl-sulfoximine of step A were converted into 3.54 g (37% over all) of (−)-1,5-diphenyl-1H-1,2,4-thiadiazine-1-oxide melting at 102°–103° C. from ether with a specific rotation of $[\alpha]_D^{20} = -120.7°$ (c=4.1% in acetone).

EXAMPLE 19

(+)-1,5-diphenyl-1H-1,2,4-thiadiazine-1-oxide

Step A: (−)-S-methyl-S-phenyl-sulfoximine

Using the procedure of Step A of Example 18 (−)-S-methyl-S-phenyl-sulfoximine was prepared by resolution of the crude (80–85%) (−)-S-methyl-S-phenyl-sulfoximine obtained as a by-product of the preparation of Step A of example 18 above by crystallization as the salt of 1-10 camphorsulfonic acid from acetone $[\alpha]_D^{20} = -36.1°$ (c=4.2, acetone).

Step B: (+)-1,5-diphenyl-1H-1,2,4-thiadiazine-1-oxide

Using the method of Example 18, (−)-S-methyl-S-phenylsulfoximine of Step A above was converted into (+)-1,5-diphenyl-1H-1,2,4-thiadiazine-1-oxide with a specific rotation of $[\alpha]_D^{20} = +119.4°$ (c=4.1% in acetone).

EXAMPLE 20

(+)-3-methoxy-1,5-diphenyl-1H-1,2,4-thiadiazine-1-oxide

Using the method for the preparation of S-(2-aminostyryl)-S-phenyl-sulfoximine (Example 1), 3-hydroxy-1,5-diphenyl-1H-1,2,4-thiadiazine-1-oxide (Example 7), 3-chloro-1,5-diphenyl-1H-1,2,4-thiadiazine-1-oxide (Example 9, Step A) and 3-methoxy-1,5-diphenyl-1H-1,2,4-thiadiazine-1-oxide (Example 14), 8.5 g (55 mmole) of (+)-S-methyl-S-phenyl-sulfoximine (Example 18, Step A) were converted into 3.2 g (20% over all) of (+)-3-methoxy-1,5-diphenyl-1H-1,2,4-thiadiazine-1-oxide melting at 134°–135° C. after crystallization from ether with a specific rotation of $[\alpha]_D^{20} = +123.9°$ (c=2% in acetone).

TABLE I

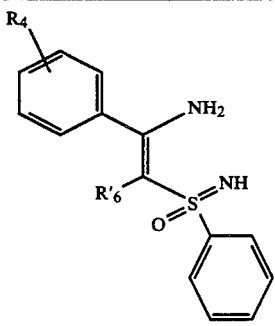

| Preparation | R'$_6$ | R$_4$ | Yield % | Mp. °C. | IR.cm$^{-1}$ (KBr disc) | H'nmr (CDCl$_3$ - ppm relative to TMS) |
|---|---|---|---|---|---|---|
| 1 | H | H | 64 | 95–96 | 3420, 3320, 1620, 1550, 1445 | δ3.2(s, 1H, =NH); δ4.95(s, 1H, H–C(=O)–); δ6.4(s, 2H, —NH$_2$); δ7.3–8.1(m, 10H, aryl—H) |
| 2 | H | 4-CH$_3$— | 61 | Oil* | 3395, 3290, 1652, 1545, 1515 | δ2.3(s, 3H, aryl CH$_3$); δ2.9(s, 1H, =NH); δ4.9(s, 1H, H–C(=O)–); δ6.45(s, 2H, —NH$_2$); δ7–8.1(m, 9H, aryl—H) |
| 3 | H | 4-CH$_3$O— | 68 | Oil* | 3420, 3310, 1620, 1545, 1510 | δ3.0(s, 1H, =NH); δ3.8(s, 3H—OCH$_3$); δ4.9(s, 1H, H–C(=O)–); δ6.4(s, 2H.—NH$_2$); δ6.9(d, J=9, 2H, aryl H O— to OCH$_3$); δ7.4–8(m, 7H aryl H) |
| 4 | H | 2-Cl— | 29 | Oil* | 3410, 3320, 1620, 1555, 1450 | δ2.8(s, 1H, NH); δ4.65(s, 1H, H–C(=O)–); δ6.4(s, 2H, NH$_2$); δ7–8.1(m, 9H, aryl—H) |
| 5 | CH$_3$ | H | 43 | Oil* | 3420, 3320, 1615, 1570, 1445 | δ1.6(s, 3H, —CH$_3$); δ3.3(s, 1H, =NH); δ6.35(s, 2H, NH$_2$); δ7.3–8.2(m, 10H, aryl H) |

*Not readily crystallised, used as an oil in the next stage without further purification.

TABLE II

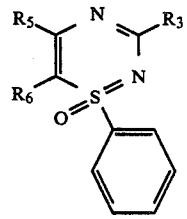

(I)

| Example | R$_3$ | R$_5$ | R$_6$ | Yield % | Mp. °C. | Formula | M. Wt. |
|---|---|---|---|---|---|---|---|
| 1 | —H | Phenyl | —H | 80 | 110–111 | C$_{15}$H$_{12}$N$_2$OS | 268.32 |
| 2 | —H | CH$_3$—C$_6$H$_4$— | —H | 74 | 103–103.5 | C$_{16}$H$_{14}$N$_2$OS | 282.35 |
| 3 | —H | CH$_3$O—C$_6$H$_4$— | —H | 57 | 102–104 | C$_{16}$H$_{14}$N$_2$O$_2$S | 298.34 |

TABLE II-continued $$\text{(I)}$$

Structure (I): R5 and N attached to a ring with R3; R6 and S(=O) attached; S connected to N-phenyl.

| Ex | R6 | R5 | R3 | Yield % | mp °C | Formula | MW |
|---|---|---|---|---|---|---|---|
| 4 | —H | 2-Cl-phenyl | —H | 79 | 85–87 | $C_{15}H_{11}ClN_2OS$ | 302.76 |
| 5 | —H | Phenyl | —CH$_3$ | 75 | 105–106 | $C_{16}H_{14}N_2OS$ | 282.35 |
| 6 | —CH$_3$ | Phenyl | —H | 86 | 103–104 | $C_{16}H_{14}N_2OS$ | 282.35 |
| 7 | —OH | Phenyl | —H | 84 | 304–305 | $C_{15}H_{12}N_2O_2S$ | 284.32 |
| 8 | —NH$_2$ | Phenyl | —H | 21 | 169–170 | $C_{15}H_{13}N_3OS$ | 283.34 |
| 9 | —NH$_2$ | Phenyl | —H | 93 | 169–170 | $C_{15}H_{13}N_3OS$ | 283.34 |
| 10 | —N(piperidinyl) | Phenyl | —H | 61 | 164–165 | $C_{20}H_{21}N_3OS$ | 351.47 |
| 11 | —N(4-NCH$_3$-piperazinyl) | Phenyl | —H | 50 | 193–194 | $C_{20}H_{22}N_4OS$ · 0.25H$_2$O | 370.99 |
| 12 | —OEt | Phenyl | —H | 74 | 105–107 | $C_{17}H_{16}N_2O_2S$ | 312.39 |
| 13 | —H | Phenyl | —Br | 42 | 135–136 | $C_{15}H_{11}BrN_2OS$ | 347.24 |
| 14 | OCH$_3$ | Phenyl | H | 72 | 99–101 | $C_{16}H_{14}N_2O_2S$ | 298.36 |
| 15 | SCH$_3$ | Phenyl | H | 74 | 148–150 | $C_{16}H_{14}N_2OS_2$ | 314.43 |
| 16 | SEt | Phenyl | H | 66 | 78–79 | $C_{17}H_{16}N_2OS_2$ | 328.44 |
| 17 | —CF$_3$ | Phenyl | H | 70 | 136–137 | $C_{16}H_{11}N_2OSF_3$ | 336.32 |
| 18 | H | Phenyl | H | 37+ | 102–103 | $C_{15}H_{12}N_2OS$ | 268.32 |
| 19 | H | Phenyl | H | 52+ | 101–103 | $C_{15}H_{12}N_2OS$ | 268.32 |
| 20 | —OCH$_3$ | Phenyl | H | — | 134–135 | $C_{16}H_{14}N_2O_2S$ | 298.36 |

| Example | Analysis Calculated/Found C | H | N | S | Other | IR (KBr disc) cm$^{-1}$ | $^1$H NMR* (ppm relative to tetramethylsilane) |
|---|---|---|---|---|---|---|---|
| 1 | 67.14 / 67.22 | 4.51 / 4.63 | 10.44 / 10.34 | 11.95 / 11.73 | — | 3070, 1590, 1540, 1500 | δ6.2 (d, J=1.5, 1H); δ7.2–8.0 (m, 10H); δ8.3 (d, J=1.5, 1H) |
| 2 | 68.06 / 67.81 | 5.00 / 5.05 | 9.92 / 9.93 | 11.36 / 11.25 | — | 3030, 1625, 1545, 1515 | δ2.38 (s, 3H); δ6.2 (d, J=1.5, 1H); δ7.1–8.0 (m, 10H); δ8.25 (d, J=1.5, 1H) |
| 3 | 64.41 / 64.35 | 4.73 / 4.79 | 9.39 / 9.31 | 10.75 / 10.66 | — | 3060, 1605, 1540, 1510 | δ3.8 (s, 3H); δ6.15 (d, J=1.0, 1H); δ6.9 (d, J=10, 2H), δ7.2–8.0 (m, 7H); δ8.2 (d, J=1.0, 1H) |
| 4 | 59.56 / 59.61 | 3.66 / 3.74 | 9.25 / 9.25 | 10.56 / 10.66 | Cl. 11.71 / 11.70 | 3072, 1595, 1560, 1540 | δ6.15 (d, J=2.0, 1H); δ7.1–8.0 (m, 9H); δ8.12 (d, J=2.0, 1H) |
| 5 | 68.06 / 67.78 | 5.00 / 5.02 | 9.92 / 9.77 | 11.36 / 11.33 | — | 3065, 1580, 1555 | δ1.9 (s, 3H); δ7.2–8.0 (m, 10H); δ8.07 (s, 1H) |
| 6 | 68.06 / 68.18 | 5.00 / 5.10 | 9.92 / 9.86 | 11.36 / 11.23 | — | 3095, 1580, 1530 | δ2.48 (s, 3H); δ6.07 (s, 1H); δ7.3–8.0 (m, 10H) |
| 7 | 63.34 / 63.30 | 4.26 / 4.31 | 9.86 / 9.88 | 11.28 / 11.24 | — | 3170, 3060, 2950, 1650, 1600 1575 | (D$_6$-DMSO) δ6.5 (s, 1H); δ7.4–8.1 (m, 10H); δ10.82 (s, 1H exchanges with D$_2$O) |
| 8 | 63.58 / 63.47 | 4.62 / 4.67 | 14.83 / 14.73 | 11.32 / 11.17 | — | 3430, 3295, 3100, 1630, 1540 | δ2.45 (bs, approx 0.4H):δ5.6 (bs) and δ5.75 (s) (2.6H combined); δ7.2–8.0 (m, 10H) |
| 9 | 63.58 / 63.47 | 4.62 / 4.67 | 14.83 / 14.73 | 11.32 / 11.17 | — | 3430, 3295, 3100, 1630, 1540 | δ2.45 (bs, approx 0.4H):δ5.6 (bs) and δ5.75 (s) (2.6H combined); δ7.2–8.0 (m, 10H) |
| 10 | 68.34 / 68.00 | 6.02 / 6.13 | 11.96 / 11.98 | 9.12 / 9.02 | — | 2920, 2842, 1580 1505 | δ1.6 (bs, 6H); δ3.85 (bs, 4H); δ5.65 (s, 1H); δ7.2–8.0 (m, 10H) |
| 11 | 64.75 / 64.69 | 6.11 / 6.02 | 15.10 / 15.04 | 8.64 / 8.57 | — | 3075 2930 2680 1580 1515 | δ2.28 (s) and δ3.4 (t or dd, J=6.8, 7H combined); δ3.9 (t or dd, J=6.0, 4H); δ5.78 (s, 1H); δ7.2–8.1 (m, 10H) |
| 12 | 65.36 / 65.10 | 5.16 / 5.14 | 8.97 / 8.98 | 10.26 / 10.14 | — | 3040, 1582, 1537 | δ1.4 (t, J=7.0, 3H); δ4.45 (q, J=7.0, 2H); δ6.02 (s, 1H); δ7.3–8.0 (m, 10H) |
| 13 | 51.89 / 51.61 | 3.19 / 3.27 | 8.07 / 8.13 | 9.24 / 9.13 | Br. 23.01 / 23.08 | 1600, 1580, 1535 | δ7.1–8.1 (m, 10H); δ8.27 (s, 1H) |
| 14 | 64.41 | 4.73 | 9.39 | 10.75 | — | 1530, 1470, 1383, 1323, 1238 | δ4.05 (s, 3H); δ6.08 (s, 1H); δ7.35–8.0 (m, 10H) |
| 15 | 61.12 | 4.49 | 8.91 | 20.40 | — | 1440, 1388, 1370, 1225, 1190 | δ2.6 (s, 3H); δ6.05 (s, 1H); |

TABLE II-continued

(I)

| | | | | | | | |
|---|---|---|---|---|---|---|---|
| 16 | 62.17 | 4.91 | 8.53 | 19.52 | — | 1445, 1418, 1360, 1220, 1195 | δ7.3–8.0 (m, 10H) |
| | 62.26 | 4.94 | 8.55 | 19.50 | — | | δ1.4 (t, 3H); δ3.18 (q, 2H); |
| | | | | | | | δ6.05 (s, 1H); δ7.35–8.0 (m, 10H) |
| 17 | 57.14 | 3.30 | 8.33 | 9.53 | F. 16.95 | 1540, 1340, 1205, 1190, 1130 | δ6.38 (s, 1H); δ7.3–8.1 (m, 10H) |
| | 57.14 | 3.38 | 8.26 | 9.56 | 16.89 | | |
| 18 | 67.14 | 4.51 | 10.44 | 11.95 | — | 1525, 1445, 1400, 1230, 1190 | δ6.25 (d, J=1.5 Hz); δ7.3–8.0 (m, 10H); |
| | | | | | | | δ8.28 (d, J=1.5 Hz) |
| 19 | 67.14 | 4.51 | 10.44 | 11.95 | — | 1522, 1446, 1397, 1225, 1190 | δ6.25 (d, J=1.5 Hz); δ7.3–8.0 (m, 10H); |
| | 67.20 | 4.60 | 10.45 | 11.94 | | | δ8.28 δ (d, J=1.5 Hz) |
| 20 | 64.41 | 4.73 | 9.39 | 10.75 | — | 1530, 1472, 1387, 1325, 1240 | δ4.05 (s, 3H); δ6.08 (s, 1H); |
| | 64.24 | 4.76 | 9.36 | 10.62 | | | δ7.35–8.0 (m, 10H) |

+Yield from optically-active S—methyl-S—phenyl-sulphoximine
*J in Hz; solvent CDCl$_3$, except where shown

EXAMPLE 21

Tablets were prepared containing 25 mg of the product of Examples 1 or 5 or 10 mg of the product of Example 19 and sufficient excipient of lactose, talc, starch and magnesium stearate for a final tablet weight of 150 mg.

PHARMACOLOGICAL DATA

The anxiolytic activity was determined by modifications of the conflict method of Geller et al [Psychopharmacologia, 1960, I. 482]. The values given in Table III are the minimum effective doses at which there was an observed increase in shocks above control (MED mg/kg po).

TABLE III

| EXAMPLE | GELLER CONFLICT MED mg/kg po |
|---|---|
| 1 | 5 |
| 3 | 50 |
| 5 | 10 |
| 6 | 10 |
| 8 | 50 |
| 9 | 50 |
| 10 | 50 |
| 11 | 50 |
| 12 | 50 |
| 13 | 10 |
| 14 | 5 |
| 16 | 50 |
| 17 | 50 |
| 18 | 2 |
| 19 | 50 |
| 20 | 5 |

Various modifications of the products and method of the invention may be made without departing from the spirit or scope thereof and it is to be understood that the invention is intended to be limited only as defined in the appended claims.

What we claim is:

1. A compound selected from the group consisting of optical isomers and mixtures thereof of 1,2,4-thiadiazines of the formula

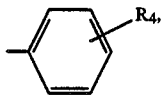

I wherein $R_3$ is selected from the group consisting of hydrogen, —OH, —CF$_3$, alkyl, alkoxy and alkylthio of 1 to 6 carbon atoms, cycloalkyl of 3 to 6 carbon atoms optionally substituted with alkyl of 1 to 6 carbon atoms and $$-N\begin{matrix}R_1\\R_2\end{matrix},$$

$R_1$ and $R_2$ are individually selected from the group consisting of hydrogen and alkyl of 1 to 3 carbon atoms or taken together with the nitrogen to which they are attached form a saturated heterocycle selected from the group consisting of pyrrolidino, piperidino, morpholino, thiomorpholino, piperazin-1-yl and 4-alkyl-piperazin-1-yl of 1 to 3 alkyl carbon atoms, $R_5$ is

[benzene ring with $R_4$ substituent]

$R_4$ is selected from the group consisting of hydrogen, halogen and alkyl and alkoxy of 1 to 3 carbon atoms, $R_6$ is selected from the group consisting of hydrogen, halogen and alkyl of 1 to 3 carbon atoms with the proviso that $R_6$ may represent halogen only when $R_3$ is hydrogen, —OH, alkyl and alkoxy of 1 to 6 carbon atoms or cycloalkyl of 3 to 6 carbon atoms optionally substituted with alkyl of 1 to 6 carbon atoms and their non-toxic, pharmaceutically acceptable acid addition salts.

2. A compound of claim 1 wherein $R_3$ is selected from the group consisting of hydrogen, hydroxy, —$CF_3$, alkyl, alkoxy and alkylthio of 1 to 6 carbon atoms, cycloalkyl of 3 to 6 carbon atoms optionally substituted with alkyl of 1 to 6 carbon atoms, —$NH_2$, mono- and di alkylamino of 1 to 3 alkyl carbon atoms, pyrrolidino, piperidino, morpholino, thiomorpholino, piperazin-1-yl and 4-alkyl-piperazin-1-yl of 1 to 3 alkyl carbon atoms, $R_5$ is selected from the group consisting of phenyl, chlorophenyl, methylphenyl and methoxyphenyl and $R_6$ is selected from the group consisting of hydrogen, bromine and methyl.

3. A compound of claim 1 wherein $R_3$ is selected from the group consisting of hydrogen, methyl, —$CF_3$, —OH, ethoxy, methylthio, ethylthio, —$NH_2$, piperidino and 4-methyl-piperazin-1-yl, $R_5$ is selected from the group consisting of phenyl, o-chlorophenyl, p-methylphenyl and p-methoxyphenyl and $R_6$ is selected from the group consisting of hydrogen, bromine and methyl.

4. A compound of claim 1 selected from the group consisting of 1,5-diphenyl-1H-1,2,4-thiadiazine-1-oxide and its non-toxic, pharmaceutically acceptable acid addition salts.

5. A compound of claim 1 selected from the group consisting of 1,5-diphenyl-6-methyl-1H-1,2,4-thiadiazine-1-oxide and its non-toxic, pharmaceutically acceptable acid addition salts.

6. A compound of claim 1 selected from the group consisting of 1,5-diphenyl-3-methyl-1H-1,2,4-thiadiazine-1-oxide and its non-toxic, pharmaceutically acceptable acid addition salts.

7. A compound of claim 1 selected from the group consisting of 6-bromo-1,5-diphenyl-1H-1,2,4-thiadiazine-1-oxide and its non-toxic, pharmaceutically acceptable acid addition salts.

8. A compound of claim 1 selected from the group consisting of 3-methoxy-1,5-diphenyl-1H-1,2,4-thiadiazine-1-oxide and its non-toxic, pharmaceutically acceptable acid addition salts.

9. A compound of claim 1 selected from the group consisting of (—)-1,5-diphenyl-1H-1,2,4-thiadiazine-1-oxide and its non-toxic, pharmaceutically acceptable acid addition salts.

10. A compound of claim 1 selected from the group consisting of (+)-3-methoxy-1,5-diphenyl-1H-1,2,4-thiadiazine-1-oxide and its non-toxic, pharmaceutically acceptable acid addition salts.

11. An anxiolytic composition comprising an anxiolytically effective amount of at least one compound of claim 1 and an inert pharmaceutical carrier.

12. A composition of claim 11 wherein in the active compound $R_3$ is selected from the group consisting of hydrogen, hydroxy, —$CF_3$, alkyl, alkoxy and alkylthio of 1 to 6 carbon atoms, cycloalkyl of 3 to 6 carbon atoms optionally substituted with alkyl of 1 to 6 carbon atoms, —$NH_2$, mono- and di alkylamino of 1 to 3 alkyl carbon atoms, pyrrolidino, piperidino, morpholino, thiomorpholino, piperazin-1-yl and 4-alkylpiperazin-1-yl of 1 to 3 alkyl carbon atoms.

13. A composition of claim 11 wherein in the active compound $R_3$ is selected from the group consisting of hydrogen, methyl, —$CF_3$, —OH, ethoxy, methylthio, ethylthio, —$NH_2$, piperidino and 4-methyl-piperazin-1-yl, $R_5$ is selected from the group consisting of phenyl, o-chlorophenyl, p-methylphenyl and p-methoxyphenyl and $R_5$ is selected from the group consisting of hydrogen, bromine and methyl.

14. A composition of claim 11 wherein the active compound is selected from the group consisting of 1,5-diphenyl-1H-1,2,4-thiadiazine-1-oxide and its non-toxic, pharmaceutically acceptable acid addition salts.

15. A composition of claim 11 wherein the active compound is selected from the group consisting of 1,5-diphenyl-6-methyl-1H-1,2,4-thiadiazine-1-oxide and its non-toxic, pharmaceutically acceptable acid addition salts.

16. A composition of claim 11 wherein the active compound is selected from the group consisting of 1,5-diphenyl-3-methyl-1H-1,2,4-thiadiazine-1-oxide and its non-toxic, pharmaceutically acceptable acid addition salts.

17. A composition of claim 11 wherein the active compound is selected from the group consisting of 6-bromo-1,5-diphenyl-1H-1,2,4-thiadiazine-1-oxide and its non-toxic, pharmaceutically acceptable acid addition salts.

18. A composition of claim 11 wherein the active compound is selected from the group consisting of 3-methoxy-1,5-diphenyl-1H,1,2,4-thiadiazine-1-oxide and its non-toxic, pharmaceutically acceptable acid addition salts.

19. A composition of claim 11 wherein the active compound is selected from the group consisting of (—)-1,5-diphenyl-1H-1,2,4-thiadiazine-1-oxide and its non-toxic, pharmaceutically acceptable acid addition salts.

20. A composition of claim 11 wherein the active compound is selected from the group consisting of (+)-3-methoxy-1,5-diphenyl-1H-1,2,4-thiadiazine-1-oxide and its non-toxic, pharmaceutically acceptable acid addition salts.

21. A method of relieving anxiety in warm-blooded animals comprising administering to warm-blooded animals an anxiolytically effective amount of at least one compound of claim 1.

22. A method of claim 21 wherein in the active compound $R_3$ is selected from the group consisting of hydrogen, hydroxy, —$CF_3$, alkyl, alkoxy and alkylthio of 1 to 6 carbon atoms, cycloalkyl of 3 to 6 carbon atoms optionally substituted with alkyl of 1 to 6 carbon atoms, —$NH_2$, mono- and di alkylamino of 1 to 3 alkyl carbon atoms, pyrrolidino, piperidino, morpholino, thiomorpholino, piperazin-1-yl and 4-alkylpiperazin-1-yl of 1 to 3 alkyl carbon atoms, $R_5$ is selected from the group consisting of phenyl, chlorophenyl, methylphenyl and methoxyphenyl and $R_6$ is selected from the group consisting of hydrogen, bromine and methyl.

23. A method of claim 24 wherein in the active compound $R_3$ is selected from the group consisting of hydrogen, methyl, —$CF_3$, —OH, ethoxy, methylthio, ethylthio, —$NH_2$, piperidino and 4-methyl-piperazin-1-yl, $R_5$ is selected from the group consisting of phenyl, o-chlorophenyl, p-methylphenyl and p-methoxyphenyl and $R_6$ is selected from the group consisting of hydrogen, bromine and methyl.

24. A method of claim 21 wherein the active compound is selected from the group consisting of 1,5-diphenyl-1H-1,2,4-thiadiazine-1-oxide and its non-toxic, pharmaceutically acceptable acid addition salts.

25. A method of claim 21 wherein the active compound is selected from the group consisting of 1,5-diphenyl-6-methyl-1H-1,2,4-thiadiazine-1-oxide and its non-toxic pharmaceutically acceptable acid addition salts.

26. A method of claim 21 wherein the active compound is selected from the group consisting of 1,5- diphenyl-3-methyl-1H-1,2,4-thiadiazine-1-oxide and its non-toxic, pharmaceutically acceptable acid addition salts.

27. A method of claim 21 wherein the active compound is selected from the group consisting of 6-bromo-1,5-diphenyl-1H-1,2,4-thiadiazine-1-oxide and its non-toxic, pharmaceutically acceptable acid addition salts.

28. A method of claim 21 wherein the active compound is selected from the group consisting of 3-methoxy-1,5-diphenyl-1H-1,2,4-thiadiazine-1-oxide and its non-toxic, pharmaceutically acceptable acid addition salts.

29. A method of claim 21 wherein the active compound is selected from the group consisting of (−)-1,5-diphenyl-1H-1,2,4-thiadiazine-1-oxide and its non-toxic, pharmaceutically acceptable acid addition salts.

30. A method of claim 21 wherein the active compound is selected from the group consisting of (+)-3-methoxy-1,5-diphenyl-1H-1,2,4-thiadiazine-1-oxide and its non-toxic, pharmaceutically acceptable acid addition salts.

* * * * *